US009606051B2

United States Patent
Kuo et al.

(10) Patent No.: US 9,606,051 B2
(45) Date of Patent: Mar. 28, 2017

(54) APPARATUS AND METHOD FOR PERFORMING A LIGHT-ABSORPTION MEASUREMENT OF A SPECIFIED AMOUNT OF SAMPLE SUBJECT TO PRESSURE FORCE

(71) Applicant: Mettler-Toledo AG, Greifensee (CH)

(72) Inventors: Chun-Hung Kuo, Alexandria, VA (US); Tomasz Pol, Severna Park, MD (US); Mario Crevatin, Winterthur (CH)

(73) Assignee: METTLER-TOLEDO GMBH, Greifensee (CH)

( * ) Notice: Subject to any disclaimer, the term of this patent is extended or adjusted under 35 U.S.C. 154(b) by 0 days.

(21) Appl. No.: 14/558,207

(22) Filed: Dec. 2, 2014

(65) Prior Publication Data

US 2016/0153895 A1    Jun. 2, 2016

(51) Int. Cl.
*G01N 21/00* (2006.01)
*G01N 21/25* (2006.01)
(Continued)

(52) U.S. Cl.
CPC .......... *G01N 21/255* (2013.01); *G01N 21/01* (2013.01); *G01N 21/0303* (2013.01);
(Continued)

(58) Field of Classification Search
CPC .......... G01N 21/31; G01N 2021/0346; G01N 21/03; G01N 21/59; B01L 9/00; B01J 3/0267
(Continued)

(56) References Cited

U.S. PATENT DOCUMENTS 4,934,816 A * 6/1990 Silver .................. G01J 3/02
250/343
5,739,432 A * 4/1998 Sinha .................. G01N 29/036
73/579
(Continued)

FOREIGN PATENT DOCUMENTS

CN        102042961 A     5/2011
DE   10 2010 048 651 B3   3/2012
(Continued)

OTHER PUBLICATIONS

Notification of Transmittal of the International Search Report (Forms PCT/ISA/220 and PCT/ISA/210) and the Written Opinion of the International Searching Authority (Form PCT/ISA/237) issued on Mar. 21, 2016 by the European Patent Office in corresponding International Application No. PCT/EP2015/077248. (15 pages).

*Primary Examiner* — Hoa Pham
(74) *Attorney, Agent, or Firm* — Buchanan Ingersoll & Rooney PC (57) ABSTRACT

An apparatus and a method are disclosed for performing a light-absorption measurement of a specified amount of sample. A method for performing a light-absorption measurement of a specified amount of sample includes placing the sample on the surface of an apparatus including the surface and a light reflector, the light reflector being mechanically coupled with the surface and separated from the surface by a separation distance, changing the separation distance, while the light reflector remains mechanically coupled with the surface, to a first separation distance, and performing a first light-absorption measurement of the sample via the apparatus, while the separation distance is equal to the first separation distance, and while the sample is subject to pressure force.

19 Claims, 4 Drawing Sheets

(51) Int. Cl.
*G01N 21/03* (2006.01)
*G01N 21/01* (2006.01)

(52) U.S. Cl.
CPC . *G01N 2021/035* (2013.01); *G01N 2021/036* (2013.01); *G01N 2021/0314* (2013.01); *G01N 2021/0364* (2013.01)

(58) Field of Classification Search
USPC .................. 356/432–440, 244, 246
See application file for complete search history.

(56) References Cited

U.S. PATENT DOCUMENTS

| | | | |
|---|---|---|---|
| 6,339,472 B1* | 1/2002 | Hafeman | G01J 3/08 |
| | | | 356/433 |
| 6,628,382 B2 | 9/2003 | Robertson | |
| 7,483,138 B2* | 1/2009 | Sahiri | G01N 21/0303 |
| | | | 356/246 |
| 8,049,884 B2 | 11/2011 | Tsukuda | |
| 8,189,199 B2 | 5/2012 | Robertson, Jr. et al. | |
| 8,223,338 B2 | 7/2012 | Robertson, Jr. et al. | |
| 8,957,387 B2* | 2/2015 | Sexton | G01N 21/59 |
| | | | 250/373 |
| 9,188,526 B2 | 11/2015 | Pfeifer et al. | |
| 2006/0077390 A1 | 4/2006 | Kralik | |
| 2006/0181710 A1* | 8/2006 | Kachanov | G01N 21/39 |
| | | | 356/437 |
| 2007/0075281 A1 | 4/2007 | Gunning et al. | |
| 2008/0106742 A1 | 5/2008 | Sahiri et al. | |
| 2008/0204755 A1 | 8/2008 | Sahiri et al. | |
| 2009/0185175 A1* | 7/2009 | Cole | G01J 1/44 |
| | | | 356/213 |
| 2010/0045980 A1 | 2/2010 | Tsukuda | |
| 2010/0085571 A1 | 4/2010 | Robertson, Jr. et al. | |
| 2010/0328652 A1 | 12/2010 | Forrer et al. | |
| 2013/0228710 A1 | 9/2013 | Pfeifer et al. | |
| 2014/0110599 A1* | 4/2014 | Lehmann | G01N 21/0303 |
| | | | 250/428 |

FOREIGN PATENT DOCUMENTS

| | | |
|---|---|---|
| EP | 2 071 317 A1 | 6/2009 |
| EP | 1 910 807 B1 | 12/2009 |
| EP | 1 743 162 B1 | 4/2010 |
| EP | 2 266 693 A1 | 12/2010 |
| JP | 02-236147 A | 9/1990 |
| WO | 2007/017035 A2 | 2/2007 |

* cited by examiner

APPARATUS AND METHOD FOR PERFORMING A LIGHT-ABSORPTION MEASUREMENT OF A SPECIFIED AMOUNT OF SAMPLE SUBJECT TO PRESSURE FORCE

FIELD

The present disclosure relates to an apparatus and method for performing a light-absorption measurement of a specified amount of sample subject to pressure force, including, but not limited to, performing a spectroscopic measurement or a photometric measurement of a micro-sample at two different path lengths of light.

BACKGROUND INFORMATION

U.S. Pat. No. 6,628,382 discloses a method and apparatus for performing spectrophotometric measurements on a sample that was pulled into a measurement column between two parallel opposing surfaces. A drop of the sample is held between the two opposing surfaces by surface tension. One of the surfaces can be controllably moved toward and away from the other. Each surface contains an optical fiber mounted coaxially with the surface and perpendicular to the surface. Each optical fiber goes through its surface and is finished flush with the surface, to provide and transmit exciting energy through the drop for measurement.

U.S. Pat. No. 8,223,338 discloses a method for performing spectrophotometric measurements on a sample pulled into a liquid column by surface tension. The sample is held between two opposing substantially parallel upper and lower surfaces by interfacial tension. The upper surface moves down so as to engage the sample, and subsequently moves upward and away from the lower surface. In this manner, interfacial tension is used to adhere the sample to the lower and upper surfaces, such that surface tension forms a liquid column of a mechanically controlled path length. The path length is controlled by a solenoid mounted below the apparatus. U.S. Pat. No. 8,189,199 discloses a similar method of forming a liquid column using surface tension.

EP Patent No. 1 743 162 B1 discloses a device having integrated beam switching systems with a detachable reflector. The device uses fiber optics for guiding light used in analysis of a liquid medium in a spectrophotometer, a spectrofluorometer or a similar measuring device. The light is guided to a measuring point located on the device, which is a receiving surface for the medium, and back therefrom to a detector. The receiving surface forms a flat measuring point on an upper side of the device and is closed by a cover-type detachable reflector in a position of use. The reflector is in close contact with a sample of the medium and can be removed before application of the sample and for cleaning the measuring point.

EP Patent No. 1 910 807 B1 discloses a device for performing absorption measurements using a detachable reflector. The device has an upper planar portion for applying a medium, a light entry portion in a housing arranged beneath the upper planar portion and a deflector in a light beam behind the light entry portion for deflection of the light upwards to an upper planar portion where a detachably mounted reflector is also located. The deflector is designed such that a direction of an optical axis of a deflected light beam is oriented upwards toward a middle of the device, and an inclined position of the optical axis of the light beam with regard to the device mid-point is arranged to be directed at a position of the reflector through which a longitudinal median between the light entry portion and a light exit from the device extends.

SUMMARY

An apparatus is disclosed for performing a light-absorption measurement of a specified amount of sample subject to pressure force. The apparatus comprises: a surface configured to receive a sample thereon; a light reflector mechanically coupled with the surface and separated from the surface by a separation distance; an actuator connected to at least one of the surface and the light reflector to change the separation distance, while the light reflector remains mechanically coupled with the surface, to a first separation distance and to a second separation distance different from the first separation distance; a first stopping member arranged to stop a first change in the separation distance at the first separation distance; and a second stopping member arranged to stop a second change in the separation distance at the second separation distance.

A method is disclosed for performing a light-absorption measurement of a specified amount of sample. The method comprises: placing the sample on the surface of an apparatus including the surface and a light reflector, the light reflector being mechanically coupled with the surface and separated from the surface by a separation distance; changing the separation distance, while the light reflector remains mechanically coupled with the surface, to a first separation distance; and performing a first light-absorption measurement of the sample via the apparatus, while the separation distance is equal to the first separation distance, and while the sample is subject to pressure force.

BRIEF DESCRIPTION OF THE DRAWINGS

Other features and advantages disclosed herein will become more apparent from the following detailed description of exemplary embodiments when read in conjunction with the attached drawings, wherein.

DETAILED DESCRIPTION

FIGS. 1 and 2A-C show exemplary embodiments of an apparatus 100 for performing a light-absorption measurement of a specified amount of sample subject to pressure force. The apparatus 100 includes a surface 102 configured to receive a sample S thereon. For example, the surface 102 is an upper surface of a base member 103. A light reflector 104 is mechanically coupled with the surface 102 and separated from the surface 102 by a separation distance. As such, the separation distance is defined as the shortest distance between the light reflector 104 and the surface 102. The light reflector 104 has at least one reflective surface. An actuator 106 is connected to at least one of the surface 102 and the light reflector 104 to change the separation distance, while the light reflector 104 remains mechanically coupled with the surface 102, to a first separation distance and to a second separation distance different from the first separation distance. A first stopping member 108 is arranged to stop a first change in the separation distance at the first separation distance, and a second stopping member 110 is arranged to stop a second change in the separation distance at the second separation distance.

Figure 1:
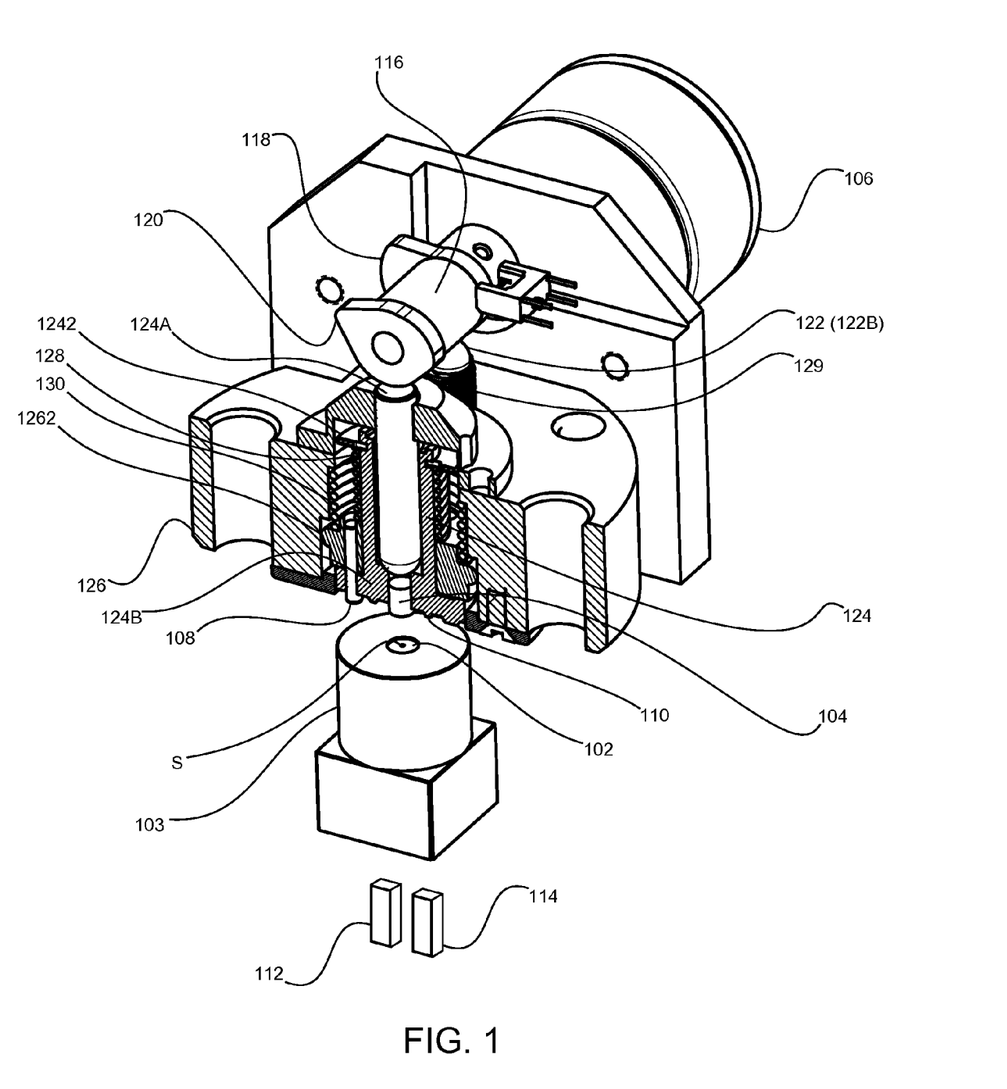
FIG. 1 shows an exemplary embodiment of an apparatus for performing a light-absorption measurement of a specified amount of sample subject to pressure force.
Figures 2A, 2C:
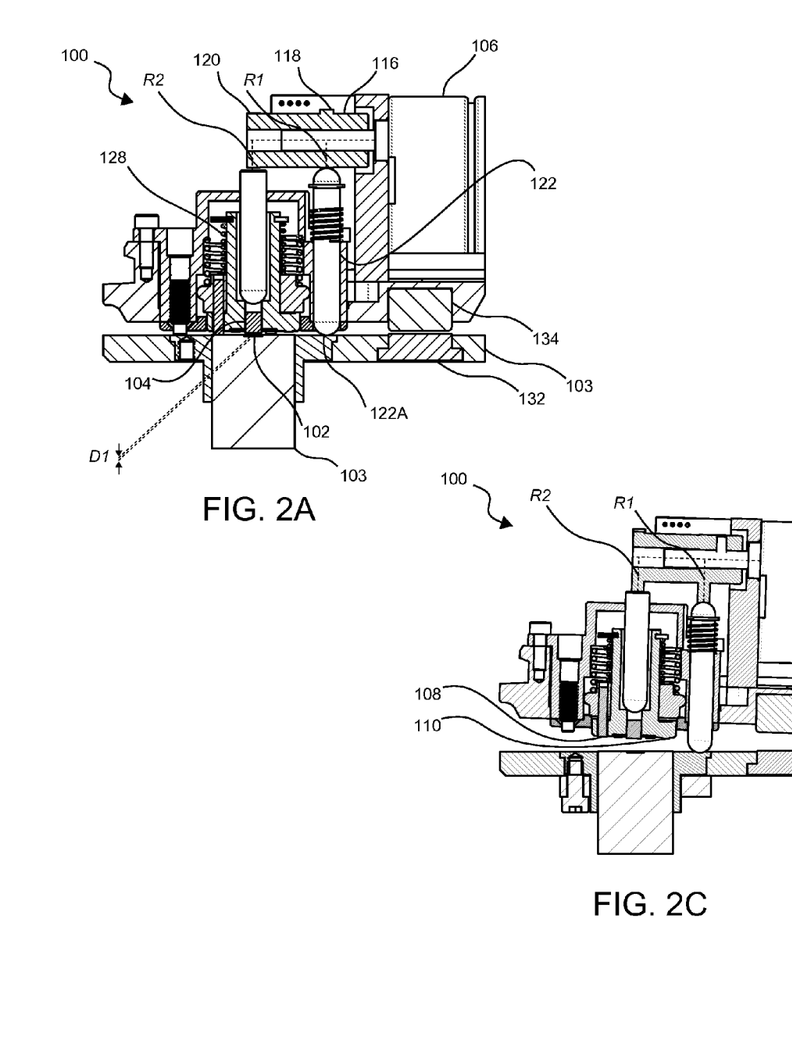
FIG. 2A shows an exemplary embodiment of an apparatus for performing a light-absorption measurement of a specified amount of sample subject to pressure force when the separation distance is equal to a distance D1.
FIG. 2C shows an exemplary embodiment of an apparatus for performing a light-absorption measurement of a specified amount of sample subject to pressure force when the light reflector and the sample surface are accessible for cleaning by a user.
Figure 2B:
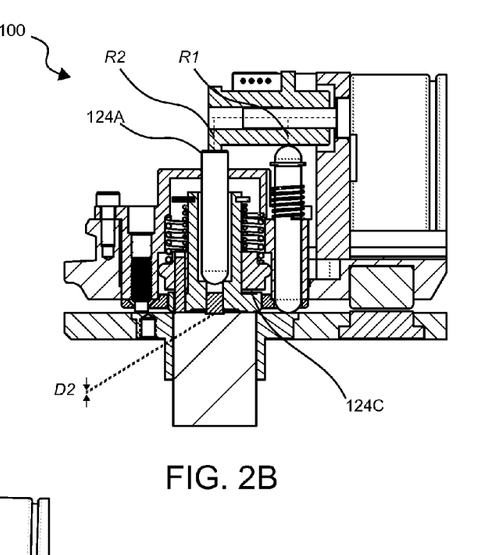
FIG. 2B shows an exemplary embodiment of an apparatus for performing a light-absorption measurement of a specified amount of sample subject to pressure force when the separation distance is equal to a distance D2.

FIG. 1 shows an exemplary embodiment of the apparatus 100. FIG. 2A shows an exemplary embodiment of the apparatus 100 when the separation distance is equal to a distance D1. FIG. 2B shows an exemplary embodiment of the apparatus 100 when the separation distance is equal to a distance D2.

FIG. 2C shows an exemplary embodiment of the apparatus 100 when the light reflector 104 and the surface 102 are accessible for cleaning by a user. In this configuration, the various components of the apparatus 100 are arranged to allow horizontal access to the light reflector 104, thereby facilitating cleaning of the light reflector 104 and the surface 102. For example, a cam arrangement on a rotatable shaft 116 of the actuator 106 is configured such that the housing 126 is moved away from the surface 102 and the light reflector 104 projects downward from the housing.

FIGS. 1 and 2A-C illustrate exemplary mechanical couplings between the light reflector 104 and the surface 102.

In exemplary embodiments of the apparatus 100, a mechanical coupling between the light reflector 104 and the surface 102 includes a base member 103, a housing 126, a sample link member 122 having first and second ends 122A and 122B, a rotatable shaft 116 of the actuator 106, the rotatable shaft 116 having first and second cam profiles 118 and 120, and a light reflector link member 124 having first and second ends 124A and 124B. The surface 102 is an upper surface of the base member 103, and the base member 103 is in contact with the first end 122A of the sample link member 122. The second end 122B of the sample link member 122 interacts with the first cam profile 118 of the rotatable shaft 116, the rotatable shaft 116 is fixed to the housing 126 and is rotatable relative to the housing 126, and the light reflector link member 124 is fixed to the light reflector 104. In some exemplary embodiments, the light reflector 104 is fixed to the second end 124B of the light reflector link member 124. Alternatively, the second end 122B of the sample link member 122 is directly attached or indirectly attached (i.e. attached via another component) to the surface 102. Alternatively, the second end 122B of the sample link member 122 and the surface 102 are arranged in any suitable manner such that as the separation distance changes, the sample link member 122 and the surface 102 do not move relative to one another.

In exemplary embodiments of the apparatus 100, the sample S has a volume in a range of 1 microliter to 10 microliters, such as a volume in a range of 1 microliter to 3 microliters, but the sample S is not limited to this volume range. For example, the sample S can have any suitable sample volume, which can include values smaller than 1 microliter and/or greater than 10 microliters.

In an exemplary embodiment of the apparatus 100, the sample S is subject to pressure force. In some embodiments, pressure force can lead to compression, spreading, and/or displacement of the sample S, unlike tension force, which could lead to stretching of a sample. Stretching the sample into a column could result in a portion of the sample having a smaller diameter. This could lead to light leaking out of the sample, thereby deteriorating the measurement being performed. By using pressure force, the risk of light leaking out of the sample is reduced. For example, in some embodiments the sample S is subject to pressure force by a portion of the surface 102 and/or a portion of the light reflector 104, causing the sample S to be compressed, to spread, and/or to displace.

In exemplary embodiments of the apparatus 100, when the rotatable shaft 116 is oriented in a first orientation (as shown in FIG. 2A), the mechanical coupling between the light reflector 104 and the surface 102 includes the housing 116, which contacts an upwardly-facing surface 124C of the light reflector link member 124.

In exemplary embodiments of the apparatus 100, when the rotatable shaft 116 is oriented in a second orientation (as shown in FIG. 2B), the mechanical coupling between the light reflector 104 and the surface 102 includes the second cam profile 120 of the rotatable shaft 116, which interacts with the first end 124A of the light reflector link member 124. The interactions between the link members and the cam profiles and/or the housing 126 can include, but are not limited to, direct or indirect (i.e. via another component) physical contact and/or magnetic attraction and/or repulsion.

In an exemplary embodiment of the apparatus 100, the surface 102 can be flat, curved, or of any desired shape. For example, the surface 102 is a flat tray surface configured to receive a sample S.

In an exemplary embodiment of the apparatus 100, the first stopping member 108 is arranged to stop a first reduction in the separation distance at the first separation distance, and the second stopping member 110 arranged to stop a second reduction in the separation distance at the second separation distance. As such, the first change in the separation distance is a first reduction in the separation distance, and the second change in the separation distance is a second reduction in the separation distance. Alternatively, the first and second changes in the separation distance can both be increases in the separation distance, or one can be a reduction and the other can be an increase, so long as the sample S remains subject to pressure force. By subjecting the sample S to pressure force, the sample S is less likely to be subject to ambient conditions, and is less likely to vibrate or otherwise change position. As a result, subjecting the sample S to pressure force can result in more desirable, repeatable, and accurate light-absorption measurements. For example, a sample S placed on the surface 102 is subject to pressure force between the surface 102 and the light reflector 104 while these changes are occurring. The first and second stopping members allow for an open-loop operation of the apparatus 100.

In an exemplary embodiment of the apparatus 100, the light reflector 104 is configured to reflect ultraviolet light and visible light onto a sample S. Alternatively, the light reflector 104 can be arranged to reflect light of any suitable range or ranges of wavelength onto a sample S. The light reflector 104 can include or be combined with a filter than transmits or blocks light from any suitable range or ranges of wavelengths. Alternatively, the light reflector 104 can include or be combined with a material that reflects light from any suitable range or ranges of wavelengths. The light reflector 104 of the apparatus 100 can provide a light pathlength of at least twice the thickness of the sample S, since light originating from a source below the surface 102 is reflected by the light reflector 104 and thus travels the separation distance twice during one measurement. As a result, a smaller amount (e.g., half) of the sample S can be sufficient for a light-absorption measurement.

An exemplary embodiment of the apparatus 100 includes a source 112 of at least one of ultraviolet light, visible light and/or infrared light. Alternatively, the source 112 can be a source of light from any suitable range or ranges of wavelengths.

An exemplary embodiment of the apparatus 100 includes a sensor 114 disposed such that the surface 102 is disposed between the light reflector 104 and the sensor 114.

In an exemplary embodiment of the apparatus 100, the actuator 106 includes a rotatable shaft 116 having a first cam profile 118 at a first axial position and a second cam profile 120 at a second axial position, the rotatable shaft 116 being connected for rotation by the actuator 106. The cams can be mechanical cams, magnetic cams, or any suitable cam element known in the art. The cams provide a controlled descent of the light reflector 104 toward the sample S, thereby avoiding splashing. The cams also provide a controlled sequence of successive long- and short-pathlength measurements, and subsequently push out the light reflector 104 so that the light reflector 104 and the surface 102 are easily accessible for cleaning.

An exemplary embodiment of the apparatus 100 for performing a spectroscopic measurement includes a sample link member 122 and a light reflector link member 124. The sample link member 122 has a first end 122A and a second end 122B. The first end 122A is fixedly linked to or in contact with the surface 102, and the second end 122B interacts with the first cam profile 118 of the rotatable shaft 116. A light reflector link member 124 has a first end 124A and a second end 124B, and the first end 124A interacts with the second cam profile 120 of the rotatable shaft 116. The light reflector 104 is disposed on the second end 124B of the light reflector link member 124. The interactions between the link members and the cam profiles can include, but are not limited to, direct or indirect physical contact and/or magnetic attraction and/or repulsion.

In exemplary embodiments of the apparatus 100, as the rotatable shaft 116 rotates, the radius R1 of the first cam profile 118 of the rotatable shaft 116 at the contact point between the first cam profile 118 and the second end 122B of the sample link member 122 changes to vary a distance between the rotatable shaft 116 and the surface 102. As this radius R1 increases (e.g., as it would from FIG. 2B to FIG. 2C), the distance between the shaft 116 and the sample link member 122 increases. Since the sample link member 122 is fixedly linked to or in contact with the surface 102, the distance between the surface 102 and the rotatable shaft 116 also increases. As the radius R1 of the first cam profile 118 at the contact point decreases (e.g., from FIG. 2C to FIG. 2B), gravity and/or magnetic forces bring the rotatable shaft 116 down from its position shown in FIG. 2C, closer to the sample link member 122, and therefore closer to the surface 102 as shown in FIG. 2B. For example, the two magnets 132 and 134 shown in FIGS. 2A-C and the weight of the upper portion of the apparatus 100 bring the rotatable shaft 116 down closer to the surface 102. Alternatively, the rotatable shaft 116 and the sample link member 122 are biased toward one another such that the distance between them is reduced as the radius R1 decreases. For example, a biasing element 129 reduces the distance between the shaft 116 and the sample support member 122

In exemplary embodiments of the apparatus 100, as the rotatable shaft 116 rotates, the radius R2 of the second cam profile 120 of the rotatable shaft 116 at the contact point between the second cam profile 120 and the first end 124A of the light reflector link member 124 changes to vary a distance between the rotatable shaft 116 and the light reflector 104. As this radius R2 increases (e.g., from FIG. 2A to FIG. 2B), the distance between the shaft 116 and the light reflector link member 124 increases. Since the light reflector 104 is disposed on the second end 124B of the light reflector link member 124, the distance between the light reflector 104 and the rotatable shaft 116 also increases. As the radius R2 of the second cam profile 120 at the contact point decreases (e.g., from FIG. 2B to FIG. 2A), a biasing element reduces the distance between the shaft 116 and the light reflector link member 124. For example, a compression spring 128 disposed between a flange 1242 of the light reflector link member 124 and a ring 1262 fixed to the housing 126 biases the light reflector link member 124 from its position shown in FIG. 2B toward its position shown in FIG. 2A. The ring 1262 depicted in FIGS. 1 and 2A-C is attached to the housing 126 by an adjustment spring 130.

In an exemplary embodiment of the apparatus 100, the contact between the first stopping member 108 and the surface 102 maintains the first separation distance D1 as shown in FIG. 2A, so that a light-absorption measurement can be performed at that distance.

In an exemplary embodiment of the apparatus 100, the contact between the second stopping member 110 and the surface 102 maintains the second separation distance D2 as shown in FIG. 2B, so that a light-absorption measurement can be performed at that distance.

An exemplary embodiment of the apparatus 100 includes first and second magnets 132 and 134. The first magnet is disposed on the base member 103, and the second magnet 134 is disposed on the housing 126. The first and second magnets 132 and 134 are configured to reduce the risk of an abrupt contact between the housing 126 and the base member 103 as the housing 126 is moved toward the base member 103. An abrupt contact could disturb the sample S and undesirably affect light-absorption measurements. In some exemplary embodiments, as shown in FIGS. 2A-C, the first and second magnets 132 and 134 do not make contact as the separation distance is changed from D1 to D2, and as the apparatus 100 is moved to a cleaning position.

In exemplary embodiments of the apparatus 100, the actuator 106 can be connected to change a separation distance between the actuator 106 and the surface 102, and/or change a separation distance between the actuator 106 and the light reflector 104. The actuator 106 can cause any one of the surface 102, the light reflector 104, and/or the actuator 106 to be displaced relative to a user.

In exemplary embodiments of the apparatus 100, the first stopping member 108 and/or the second stopping member 110 can be fixed to or integral with a particular feature of the apparatus. For example, the stopping members can include one or more pins attached to the particular feature. Possible attachments between the pins and the feature include, but are not limited to, bolting, press-fitting, gluing, welding, or any other attachments known in the art. Alternatively, the stopping members can include one or more projections that are integral with the particular feature. For example, the first stopping members 108 can include three pins, and the second stopping members 110 can include three projections. Alternatively, the stopping members can include any stops known in the art.

An exemplary embodiment of the apparatus 100 includes a sample link member 122 fixedly linked to or in contact with the surface 102, and a light reflector link member 124 fixedly linked to the light reflector 104. The first stopping member 108 is fixed to or integral with the housing 126 and is arranged to make contact with the surface 102 or the sample link member 122 such that the separation distance will be equal to the first separation distance D1. An ordinarily skilled artisan will appreciate that the first stopping member 108 stops a relative displacement of the sample link member 122 with respect to the light reflector 104.

In exemplary embodiments of the apparatus 100, the first stopping member 108 is fixedly linked to the housing 126, and stops the sample link member 122 by making contact with the sample link member 122, or alternatively any feature that is fixedly linked to the sample link member 122, including, but not limited to, the surface 102.

In alternative exemplary embodiments of the apparatus 100, the first stopping member 108 is instead fixedly linked to the surface 102.

In an exemplary embodiment of the apparatus 100, the second stopping member 110 is fixed to or integral with the light reflector link member 124 and is arranged to make contact with the surface 102 or the sample link member 122 such that the separation distance will be equal to the second separation distance D2. An ordinarily skilled artisan will appreciate that the second stopping member 110 stops a relative displacement of the light reflector link member 124 with respect to the surface 102.

In exemplary embodiments of the apparatus 100, the second stopping member 110 is fixedly linked to the light reflector link member 124, and stops the light reflector link member 124 by making contact with the sample link member 122, or alternatively any feature that is fixedly linked to or in contact with the sample link member 122, including, but not limited to, the surface 102.

In alternative exemplary embodiments of the apparatus 100, the second stopping member 110 is instead fixedly linked to the surface 102.

In exemplary embodiments of the apparatus 100, the first stopping member 108 includes pins that are fixed to the light reflector link member 124. The other end of each pin makes contact with the surface 102 or an adjacent surface to stop at the first separation distance D1 as shown in FIG. 2A. The second stopping member 110 includes projections on the light reflector link member 124. These projections make contact with the surface 102 or an adjacent surface to slop at the second separation distance D2 as shown in FIG. 2B.

An exemplary embodiment of the apparatus 100 can include a power supply connected to drive the actuator 106. Alternatively, the actuator 106 can be manual. In some exemplary embodiments, the actuator 106 includes a motor connected to the power supply.

An exemplary embodiment of the apparatus 100 includes a housing 126, wherein the actuator 106 is connected to the at least one of the surface 102 and the light reflector 104 to change the separation distance while the light reflector 104 remains at least partially disposed in the housing 126 so that the light reflector 104 is protected from external disturbances. For example, the light reflector 104 can be protected from a user bumping into the apparatus 100 and affecting the position and/or state of the light reflector 104.

An exemplary embodiment of the apparatus 100 includes a housing 126 configured to shield the surface 102 from ambient conditions. The housing 126 can hermetically seal the surface 102 and/or the light reflector 104. Alternatively, the housing 126 can act as a shield protecting at least a portion of the surface 102 and/or the light reflector 104 from, for example, ambient particle contamination, or a user bumping into the sample.

In an exemplary embodiment of the apparatus 100, a housing 126 can be closed or partially open. The housing 126 can cover a portion or the entirety of one or more components of the apparatus 100.

An exemplary embodiment of the apparatus 100 can be configured in combination with a sample S placed on the surface 102.

In exemplary embodiments of the apparatus 100, additional stopping members can be arranged on the apparatus 100 and configured to stop the change in the separation distance between the light reflector 104 and the surface at various additional separation distance increments.

Figure 3:
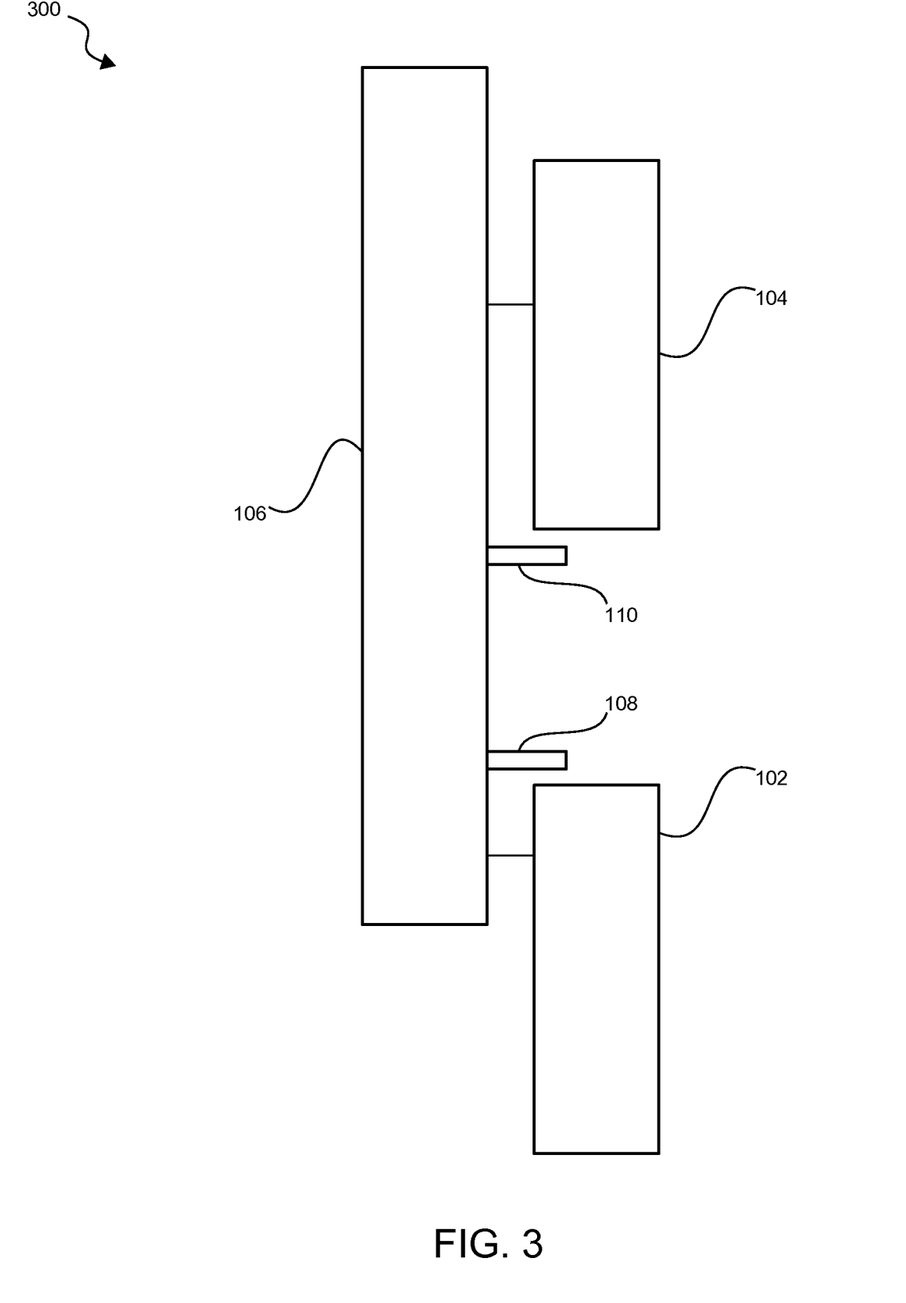
FIG. 3 shows a block diagram of an exemplary embodiment of an apparatus for performing a light-absorption measurement of a specified amount of sample subject to pressure force.

FIG. 3 shows a block diagram of an exemplary embodiment of an apparatus 300 for performing a light-absorption measurement of a specified amount of sample subject to pressure force. The apparatus 300 includes a surface 102 configured to receive a sample S thereon, a light reflector 104 mechanically coupled with the surface 102 and separated from the surface 102 by a separation distance. An actuator 106 is connected to at least one of the surface 102 and the light reflector 104 to change the separation distance, while the light reflector 104 remains mechanically coupled with the surface 102, to a first separation distance and to a second separation distance different from the first separation distance. A first stopping member 108 can be arranged to stop a first change in the separation distance at the first separation distance, and a second stopping member 110 can be arranged to stop a second change in the separation distance at the second separation distance. The actuator 106 can be operated by any combinations of manual, electric and software operations. For example, a processor can be configured to execute commands stored on non-transitory computer-readable media to control the position of the actuator 106 and/or the stopping members 108 and 110.

In exemplary embodiments of the apparatus 300, additional stopping members can be arranged on the apparatus 300 and configured to stop the change in the separation distance between the light reflector 104 and the surface at various additional separation distance increments. Alternatively, the actuator 106 can be configured to stop at various separation distances.

Figure 4:
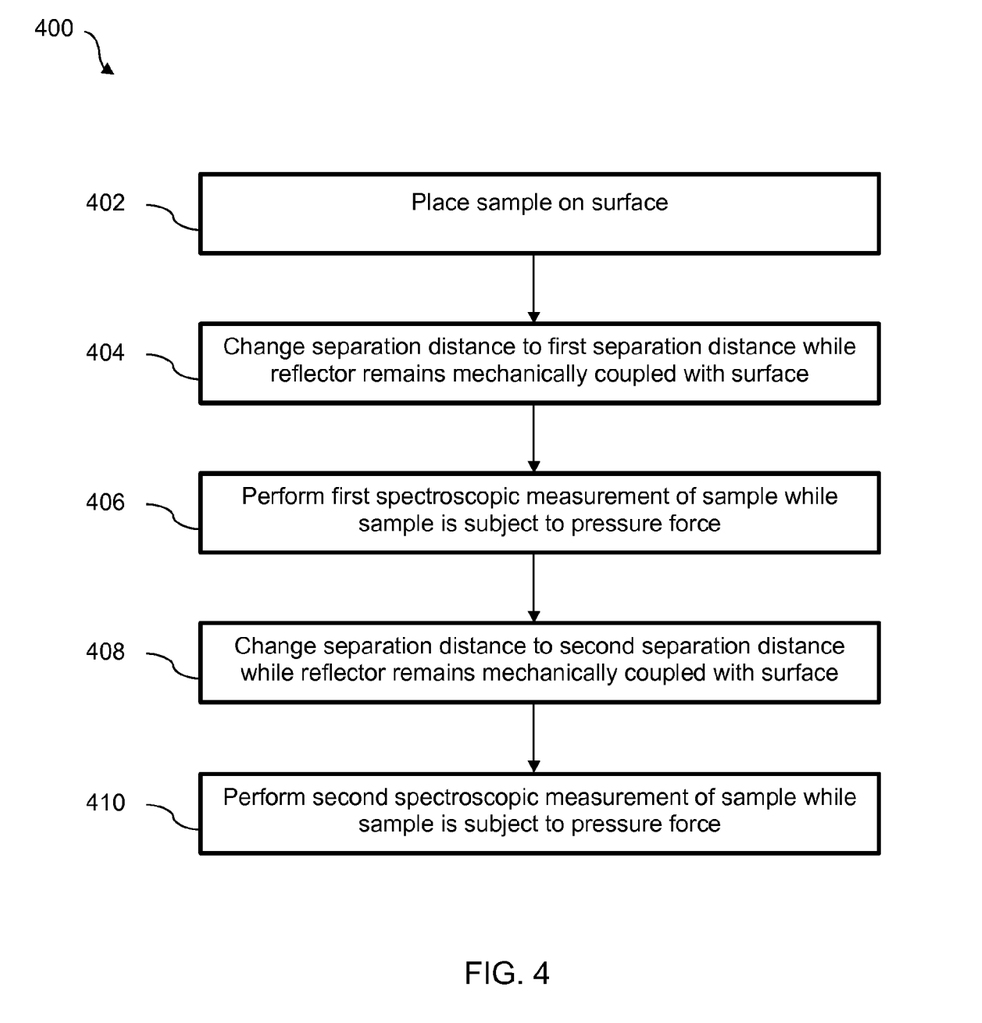
FIG. 4 shows a block diagram of an exemplary method for performing a light-absorption measurement of a specified amount of sample subject to pressure force.

FIG. 4 shows a block diagram of an exemplary method 400 for performing a light-absorption measurement of a specified amount of sample S subject to pressure force. The method 400 includes placing the sample S on the surface 102 of an apparatus 100 including the surface 102 and a light reflector 104, the light reflector 104 being mechanically coupled with the surface 102 and separated from the surface 102 by a separation distance, at step 402. The method 400 includes changing the separation distance, while the light reflector 104 remains mechanically coupled with the surface 102, to a first separation distance, at step 404, and performing a first light-absorption measurement of the sample S via the apparatus 100, while the separation distance is equal to the first separation distance, and while the sample S is subject to pressure force, at step 406. This change in separation distance can be an increase or a reduction, so long as the sample S remains subject to pressure force. By subjecting the sample S to pressure force, the sample S is less likely to be subject to ambient conditions, and is less likely to vibrate or otherwise change position. As a result, subjecting the sample S to pressure force can result in more desirable, repeatable, and accurate light-absorption measurements.

In an exemplary method 400 for performing a light-absorption measurement of a specified amount of sample S subject to pressure force, the changing of the separation distance to the first separation distance includes stopping one of the surface 102 and the light reflector 104 using a first stopping member 108 such that the separation distance is equal to the first separation distance.

An exemplary method 400 for performing a light-absorption measurement of a specified amount of sample S subject to pressure force includes changing the separation distance, while the light reflector 104 remains mechanically coupled with the surface 102, to a second separation distance different from the first separation distance, at step 408. The method 400 can include performing a second light-absorption measurement of the sample S via the apparatus 100, while the separation distance is equal to the second separation distance, and while the sample S is subject to pressure force, at step 410. This change in separation distance can be an increase or a reduction, so long as the sample S remains subject to pressure force.

In an exemplary method 400 for performing a light-absorption measurement of a specified amount of sample S subject to pressure force, the changing of the separation distance to the second separation distance can includes stopping one of the surface 102 and the light reflector 104 using a second stopping member 110 such that the separation distance is equal to the second separation distance.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description and all changes that come within the meaning and range and equivalence thereof are intended to be embraced therein.

What is claimed is:

1. An apparatus for performing a light-absorption measurement of a specified amount of sample subject to pressure force, the apparatus comprising:
    a surface configured to receive a sample thereon;
    a light reflector mechanically coupled with the surface and separated from the surface by a separation distance;
    an actuator connected to at least one of the surface and the light reflector to change the separation distance, while the light reflector remains mechanically coupled with the surface, to a first separation distance and to a second separation distance different from the first separation distance, the actuator including (i) a rotatable shaft having a first cam profile at a first axial position and a second cam profile at a second axial position, the rotatable shaft being connected for rotation by the actuator, (ii) a sample link member having a first end and a second end, the first end of the sample link member being fixedly linked to the surface, and the second end of the sample link member interacting with the first cam profile of the rotatable shaft, and (iii) a light reflector link member having a first end and a second end, the first end interacting with the second cam profile of the rotatable shaft, the light reflector being disposed on the second end of the light reflector link member;
    a first stopping member arranged to stop a first change in the separation distance at the first separation distance; and
    a second stopping member arranged to stop a second change in the separation distance at the second separation distance.

2. The apparatus for performing a light-absorption measurement of a specified amount of sample subject to pressure force according to claim 1, wherein the sample has a volume in a range of 1 microliter to 3 microliters.

3. The apparatus for performing a light-absorption measurement of a specified amount of sample subject to pressure force according to claim 1, wherein the first stopping member is arranged to stop a first reduction in the separation distance at the first separation distance, and the second stopping member is arranged to stop a second reduction in the separation distance at the second separation.

4. The apparatus for performing a light-absorption measurement of a specified amount of sample subject to pressure force according to claim 1, wherein the light reflector is configured to reflect ultraviolet light and visible light onto a sample.

5. The apparatus for performing a light-absorption measurement of a specified amount of sample subject to pressure force according to claim 1, comprising:
    a source of at least one selected from the set consisting of ultraviolet light, visible light and infrared light; and
    a sensor disposed such that the surface is disposed between the light reflector and the sensor.

6. The apparatus for performing a spectroscopic measurement according to claim 1, wherein as the rotatable shaft rotates, a radius of the first cam profile at a contact point between the first cam profile and the second end of the sample link member changes to vary a distance between the rotatable shaft and the surface.

7. The apparatus for performing a spectroscopic measurement according to claim 1, wherein as the rotatable shaft rotates, a radius of the second cam profile at a contact point between the second cam profile and the first end of the light reflector link member changes to vary a distance between the rotatable shaft and the light reflector.

8. The apparatus for performing a light-absorption measurement of a specified amount of sample subject to pressure force according to claim 1,
    wherein the light reflector link member is fixedly linked to the light reflector,
    and the first stopping member is fixed to or integral with the housing and is arranged to make contact with the surface or the sample link member such that the separation distance will be equal to the first separation distance.

9. The apparatus for performing a light-absorption measurement of a specified amount of sample subject to pressure force according to claim 8, wherein the second stopping member is fixed to or integral with the light reflector link member and is arranged to make contact with the surface or the sample link member such that the separation distance will be equal to the second separation distance.

10. The apparatus for performing a light-absorption measurement of a specified amount of sample subject to pressure force according to claim 1, the actuator comprising:
    a power supply connected to drive the actuator; and
    a motor connected to the power supply.

11. The apparatus for performing a light-absorption measurement of a specified amount of sample subject to pressure force according to claim 1, comprising:

a housing, wherein the actuator is connected to the at least one of the surface and the light reflector to change the separation distance while the light reflector remains at least partially disposed in the housing so that the light reflector is protected from external disturbances.

12. The apparatus for performing a light-absorption measurement of a specified amount of sample subject to pressure force according to claim 1, in combination with:
a sample placed on the surface.

13. An apparatus for performing a light-absorption measurement of a specified amount of sample subject to pressure force, the apparatus comprising:
a surface configured to receive a sample thereon;
a light reflector mechanically coupled with the surface and separated from the surface by a separation distance;
an actuator connected to at least one of the surface and the light reflector to change the separation distance, while the light reflector remains mechanically coupled with the surface, to a first separation distance and to a second separation distance different from the first separation distance;
a first stopping member arranged to stop a first change in the separation distance at the first separation distance; and
a second stopping member arranged to stop a second change in the separation distance at the second separation distance,
wherein a mechanical coupling between the light reflector and the surface includes a base member, a housing, a sample link member having first and second ends, a rotatable shaft of the actuator, the rotatable shaft having first and second cam profiles, and a light reflector link member having first and second ends,
wherein the surface is an upper surface of the base member, the base member is in contact with the first end of the sample link member, the second end of the sample link member interacts with the first cam profile of the rotatable shaft, the rotatable shaft is fixed to the housing and is rotatable relative to the housing, and the light reflector link member is fixed to the light reflector.

14. The apparatus for performing a light-absorption measurement of a specified amount of sample subject to pressure force according to claim 13, wherein when the rotatable shaft is oriented in a first orientation, the mechanical coupling between the light reflector and the surface includes the housing, the housing contacting an upwardly-facing surface of the light reflector link member.

15. The apparatus for performing a light-absorption measurement of a specified amount of sample subject to pressure force according to claim 13, wherein when the rotatable shaft is oriented in a second orientation, the mechanical coupling between the light reflector and the surface includes the second cam profile of the rotatable shaft, the second cam profile interacting with the first end of the light reflector link member.

16. A method for performing a light-absorption measurement of a specified amount of sample subject to pressure force, comprising:
placing a specified amount of sample on the surface of an apparatus including the surface and a light reflector, the light reflector being mechanically coupled with the surface and separated from the surface by a separation distance;
changing the separation distance, while the light reflector remains mechanically coupled with the surface, to a first separation distance, by rotating a rotatable shaft of an actuator, the actuator including (i) the rotatable shaft having a first cam profile at a first axial position and a second cam profile at a second axial position, the rotatable shaft being connected for rotation by the actuator, (ii) a sample link member having a first end and a second end, the first end of the sample link member being fixedly linked to the surface, and the second end of the sample link member interacting with the first cam profile of the rotatable shaft, and (iii) a light reflector link member having a first end and a second end, the first end interacting with the second cam profile of the rotatable shaft, and the light reflector being disposed on the second end of the light reflector link member; and
performing a first light-absorption measurement of the sample via the apparatus, while the separation distance is equal to the first separation distance, and while the sample is subject to pressure force.

17. The method for performing a light-absorption measurement of a specified amount of sample subject to pressure force according to claim 16, the changing of the separation distance to the first separation distance including:
stopping one of the surface and the light reflector using a first stopping member such that the separation distance is equal to the first separation distance.

18. The method for performing a light-absorption measurement of a specified amount of sample subject to pressure force according to claim 16, comprising:
changing the separation distance, while the light reflector remains mechanically coupled with the surface, to a second separation distance different from the first separation distance; and
performing a second light-absorption measurement of the sample via the apparatus, while the separation distance is equal to the second separation distance, and while the sample is subject to pressure force.

19. The method for performing a light-absorption measurement of a specified amount of sample subject to pressure force according to claim 18, the changing of the separation distance to the second separation distance including:
stopping one of the surface and the light reflector using a second stopping member such that the separation distance is equal to the second separation distance.

* * * * *